(12) United States Patent
Harada et al.

(10) Patent No.: US 10,154,684 B2
(45) Date of Patent: Dec. 18, 2018

(54) HAIR REGROWTH AND GROWTH PROMOTER AND USE THEREOF

(71) Applicant: PHARMA FOODS INTERNATIONAL CO., LTD., Kyoto (JP)

(72) Inventors: Seiyu Harada, Kyoto (JP); Toshio Nakamura, Kyoto (JP); Mujo Kim, Kyoto (JP)

(73) Assignee: PHARMA FOODS INTERNATIONAL CO., LTD., Kyoto (JP)

( * ) Notice: Subject to any disclaimer, the term of this patent is extended or adjusted under 35 U.S.C. 154(b) by 0 days.

(21) Appl. No.: 15/522,231

(22) PCT Filed: Oct. 30, 2015

(86) PCT No.: PCT/JP2015/080848
§ 371 (c)(1),
(2) Date: Apr. 26, 2017

(87) PCT Pub. No.: WO2016/068338
PCT Pub. Date: May 6, 2016

(65) Prior Publication Data
US 2017/0332688 A1 Nov. 23, 2017

(30) Foreign Application Priority Data

Oct. 31, 2014 (JP) ................. 2014-222303

(51) Int. Cl.
| | | |
|---|---|---|
| A23L 33/18 | (2016.01) |
| A23L 27/21 | (2016.01) |
| A61K 8/98 | (2006.01) |
| A61K 38/00 | (2006.01) |
| A61K 8/64 | (2006.01) |
| A61Q 7/00 | (2006.01) |
| A61K 35/57 | (2015.01) |
| A61K 31/00 | (2006.01) |

(52) U.S. Cl.
CPC ............ *A23L 33/18* (2016.08); *A23L 27/21* (2016.08); *A61K 8/64* (2013.01); *A61K 8/982* (2013.01); *A61K 35/57* (2013.01); *A61K 38/00* (2013.01); *A61Q 7/00* (2013.01); *A61K 31/00* (2013.01); *A61K 2800/92* (2013.01)

(58) Field of Classification Search
None
See application file for complete search history.

(56) References Cited

U.S. PATENT DOCUMENTS

2015/0164973 A1 6/2015 Kim et al.
2016/0317429 A1* 11/2016 Goralczyk ............. A61K 38/01

FOREIGN PATENT DOCUMENTS

| JP | 64-083100 | 3/1989 |
| JP | 2001328919 A | 11/2001 |
| JP | 200381866 A | 3/2003 |
| JP | 2008247874 A | 10/2008 |
| JP | 2011211979 A | 10/2011 |
| WO | WO-2006075558 A1 | 7/2006 |
| WO | WO-2009144977 A1 | 12/2009 |
| WO | WO-2014007318 A1 * | 1/2014 ........... C12Y 304/00 |

OTHER PUBLICATIONS

Mann, et al., Proteomics, 8:178. (Year: 2007).*
Translation of WO2014007318A1 translation provided by EPO. (Year: 2014).*
International Preliminary Report on Patentability for Application No. PCT/JP2015/080848, dated May 2, 2017. (English Translation).
International Search Report and Written Opinion for Application No. PCT/JP2015/080848, dated Jan. 12, 2016.
Susumu Otomo, "Hair Growth Effect of Minoxidil", Folia Pharmacol. Jpn., vol. 119, pp. 167-174 (2002).
Souad Lachgar et al., "Vascular Endothelial Growth Factor Is an Autocrine Growth Factor for Hair Dermal Papilla Cells", The Journal of Investigative Dermatology, vol. 106 No. 1, pp. 17-23 (1996).
Kang et al., "Process Development for the Recovery of Sialic Acid Fraction by Enzymatic Hydrolysis of Egg Yolk Protein," *Journal of Life Science*, vol. 15, No. 1, pp. 9-14 (2005).
Scalp Hair Care Method II, MD Journal Daily (2010). (English Translation).

* cited by examiner

*Primary Examiner* — Michael Barker
(74) *Attorney, Agent, or Firm* — Marshall, Gerstein & Borun LLP

(57) ABSTRACT

The present invention provides a hair regrowth promoter comprising an egg-yolk protein hydrolysate as an active ingredient. The egg-yolk protein hydrolysate is a safe ingredient produced from a natural source, and therefore can be widely used in daily consumable products, such as food and drink products, medicaments, animal feeds, and dietary supplements, or as a food additive, etc. The promoter etc. of the present invention can be orally administered and is thus very advantageous.

20 Claims, 4 Drawing Sheets

Specification includes a Sequence Listing.

HAIR REGROWTH AND GROWTH PROMOTER AND USE THEREOF

TECHNICAL FIELD

The present invention relates to a hair regrowth promoter and use thereof. The present invention also relates to a method for promoting hair regrowth.

BACKGROUND ART

Many people are concerned about alopecia caused by aging, genetic predisposition, social stress or other reasons. Under such circumstances, various products have been developed, including hair growers for promotion of hair growth and anti-alopecia agents for prevention of hair loss.

A known example is an anti-alopecia agent containing a soybean protein-derived peptide with a specific sequence as an active ingredient (Patent Literature 1).

The inventors have conducted studies on the functions of egg-yolk protein hydrolysates, and found that egg-yolk protein hydrolysates have antioxidant effect (Patent Literature 2), bone strengthening effect (Patent Literature 3), chondrocyte growth-promoting effect (Patent Literature 4), and other effects. However, no report has been made on hair regrowth-promoting effect of egg-yolk protein hydrolysates, which effect has no correlation with antioxidant effect, bone strengthening effect, or chondrocyte growth-promoting effect.

CITATION LIST

Patent Literature

Patent Literature 1: JP 2008-247874 A
Patent Literature 2: JP 2001-328919 A
Patent Literature 3: WO 2006/075558
Patent Literature 4: WO 2014/007318

SUMMARY OF INVENTION

Technical Problem

An object of the present invention is to provide a novel use of an egg-yolk protein hydrolysate.

Solution to Problem

The present invention was made to solve the above problem and includes the following.
(1) A hair regrowth promoter comprising an egg-yolk protein hydrolysate as an active ingredient.
(2) The promoter according to the above (1), which has a promoting effect on the production of a growth factor in hair follicle dermal papilla cells.
(3) The promoter according to the above (2), wherein the growth factor is one or more selected from the group consisting of vascular endothelial growth factor (VEGF), fibroblast growth factor-7 (FGF-7) and insulin-like growth factor-1 (IGF-1).
(4) The promoter according to any one of the above (1) to (3), which is in a form of an oral preparation.
(5) A hair regrowth-promoting medicament comprising the promoter according to any one of the above (1) to (3).
(6) A hair regrowth-promoting dietary supplement comprising the promoter according to any one of the above (1) to (3).
(7) A hair regrowth-promoting food additive comprising the promoter according to any one of the above (1) to (3).
(8) Use of an egg-yolk protein hydrolysate for production of a hair regrowth promoter.
(9) A non-therapeutic method for promoting hair regrowth, the method comprising orally administering an egg-yolk protein hydrolysate to a human in need of promotion of hair regrowth.

The present invention further includes the following.
(10) A method for promoting hair regrowth, the method comprising administering an effective amount of the promoter according to any one of the above (1) to (3) to an animal in need of promotion of hair regrowth.
(11) Use of the promoter according to any one of the above (1) to (3) for promotion of hair regrowth.
(12) The promoter according to any one of the above (1) to (3) for use in promotion of hair regrowth.
(13) A food for specified health use, a dietary supplement, a supplemental food, or a functional food, comprising the promoter according to any one of the above (1) to (3) and bearing a statement indicating hair regrowth-promoting effect.

Advantageous Effects of Invention

The present invention provides a hair regrowth promoter comprising an egg-yolk protein hydrolysate as an active ingredient. The egg-yolk protein hydrolysate is a safe ingredient produced from a natural source, and therefore can be widely used in daily consumable products, such as food and drink products, medicaments, animal feeds, and dietary supplements, or as a food additive, etc. The promoter etc. of the present invention can be orally administered and is thus very advantageous.

DESCRIPTION OF EMBODIMENTS

Figure 1:
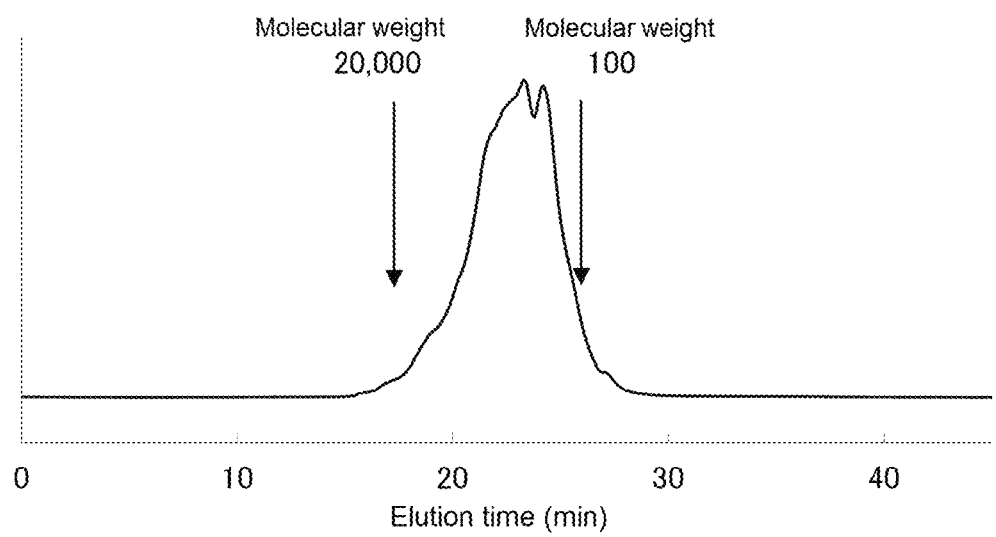
FIG. 1 is a graph showing the results of molecular weight analysis of an egg-yolk protein hydrolysate of Example 1 by gel filtration chromatography.

The present invention provides a hair regrowth promoter comprising an egg-yolk protein hydrolysate as an active ingredient.

The egg-yolk protein hydrolysate may be any egg-yolk protein hydrolysate as long as it is obtained by hydrolysis of an egg yolk protein. The egg yolk used as a raw material of the egg-yolk protein hydrolysate may be an egg yolk of chicken, duck, quail, etc., but an egg yolk of chicken is preferred to achieve high productivity. The egg yolk used herein may be in the form of an egg yolk liquid, an egg yolk powder, a defatted egg yolk powder, etc., but preferred is an egg yolk powder or a defatted egg yolk powder. For effective use of resources and high cost performance, preferred is a defatted egg yolk that is obtained as a by-product of a production process of an egg yolk oil or an egg yolk lecithin from an egg yolk. Defatting of an egg yolk is preferably performed by treating the egg yolk with an organic solvent usable for food processing (for example, at least one selected from ethanol, isopropanol, hexane, etc.). Typically, defatting of an egg yolk is carried out by adding such a solvent to an egg yolk, stirring the mixture, and collecting the resulting solids. This procedure may be repeated more than once. Ethanol is preferred to achieve convenience and safety.

The hydrolysis of an egg yolk protein is performed with the aid of an enzyme. The enzyme is not particularly limited, but preferred is an enzyme that has protease or carboxypeptidase activity and is usable for food production. Examples of the enzyme include pepsin (EC.3.4.23.1), trypsin (EC.3.4.21.4), renin (EC.3.4.23.15), rennet, which contains renin and is used for cheese making, carboxypeptidase A (EC. 3.4.17.1), proteases from *Bacillus* bacteria (trade name "Alcalase" produced by Novozymes A/S, trade name "Orientase 22BF" produced by HBI Enzymes Inc., trade name "Nukureishin" produced by HBI Enzymes Inc., trade name "Protease S 'Amano' G" produced by Amano Enzyme, Inc., trade name "THERMOASE PC10" produced by Daiwa Fine Chemicals Co., Ltd., etc.), proteases from *Aspergillus* fungi (trade name "Orientase ONS" produced by HBI Enzymes Inc., trade name "Orientase 20A" produced by HBI Enzymes Inc., trade name "Protease P 'Amano' 3G" produced by Amano Enzyme, Inc., trade name "Flavourzyme" produced by Novozymes A/S, etc.), etc. These enzymes for hydrolysis of an egg yolk protein may be used alone or in combination of two or more types. Preferred are a protease from *Bacillus* bacteria, pepsin, and a combination thereof.

The concentration of the enzyme for hydrolysis of an egg yolk protein is appropriately adjusted depending on the raw material egg yolk and the enzyme to be used. When a defatted egg yolk is used as the raw material, the mass ratio of the enzyme to the defatted egg yolk is preferably in the range between about 1:20 and about 1:1000. The enzyme reaction temperature and the reaction time also vary depending on the raw material egg yolk and the enzyme to be used. Preferably, the hydrolysis is performed at about 25 to 75° C. for about 1 to 24 hours.

The thus prepared egg-yolk protein hydrolysate may be desalted as needed and directly used. Alternatively, the egg-yolk protein hydrolysate obtained as above may be used after purification and/or fractionation by ultrafiltration, gel filtration, various column chromatographic techniques, membrane filter filtration, methods using an isoelectric point, etc. The hair regrowth-promoting effect of the egg-yolk protein hydrolysate after purification and/or fractionation can be assessed by, for example, the methods described in Examples 2 and 3.

The molecular weight distribution of the egg-yolk protein hydrolysate as determined by gel filtration chromatography is preferably such that the peak area percentage for a molecular weight range of about 100 to about 20,000 is about 65% or more of the total area of all the peaks of proteins, peptides and amino acids. More preferably, the peak area percentage is about 75% or more, further more preferably about 85% or more, further more preferably about 90% or more, of the total area.

A more preferred egg-yolk protein hydrolysate is one obtained through fractionation using an ultrafiltration membrane with a molecular weight cut-off of 1,000, wherein the molecular weight distribution of the hydrolysate as determined by gel filtration chromatography is such that the peak area percentage for a molecular weight range of about 500 to about 20,000 is about 85% or more, preferably about 90% or more, of the total area of all the peaks of proteins, peptides and amino acids.

The egg-yolk protein hydrolysate prepared as above has hair regrowth-promoting effect, hair growth-promoting effect, hair nourishing effect, anti-alopecia effect, etc. The egg-yolk protein hydrolysate is thus suitable as an active ingredient of hair regrowth promoters, hair growth promoters, hair nourishers, anti-alopecia agents, etc. Thus, the hair regrowth promoter of the present invention may also be referred to as a hair growth promoter, a hair nourisher, or an anti-alopecia agent.

The amount of the egg-yolk protein hydrolysate contained in the hair regrowth promoter of the present invention is not particularly limited, but is preferably about 0.05 to about 50% by mass, more preferably about 0.1 to about 25% by mass. The daily dose of the egg-yolk protein hydrolysate varies depending on the subject, but in cases where the subject is, for example, a human adult, the daily dose is typically about 0.05 to about 2000 mg/day, and is preferably about 0.1 to about 1000 mg/day.

The hair regrowth promoter of the present invention promotes the production of a growth factor in hair follicle dermal papilla cells. The growth factor is not particularly limited, and examples thereof include vascular endothelial growth factor (VEGF), fibroblast growth factor-7 (FGF-7), insulin-like growth factor-1 (IGF-1), etc. Preferably, the growth factor is one or more selected from the group consisting of VEGF, FGF-7, and IGF-1, and is more preferably VEGF, FGF-7, and IGF-1. The hair regrowth promoter of the present invention may also be referred to as a promoter for the production of a growth factor in hair follicle dermal papilla cells, a promoter for the production of vascular endothelial growth factor (VEGF) in hair follicle dermal papilla cells, a promoter for the production of fibroblast growth factor-7 (FGF-7) in hair follicle dermal papilla cells, or a promoter for the production of insulin-like growth factor-1 (IGF-1) in hair follicle dermal papilla cells.

The hair regrowth promoter of the present invention can be administered to a mammal via an oral or parenteral route. Examples of oral preparations include granules, powders, tablets (including sugar-coated tablets), pills, capsules, syrups, emulsions, suspensions, etc. Examples of parenteral preparations include injections (e.g., subcutaneous, intravenous, intramuscular, and intraperitoneal injections), intravenous infusions, external preparations for skin (e.g., transnasal preparations, transdermal preparations, and ointments), suppositories (for example, rectal suppositories, and vaginal suppositories), etc. These preparations can be formulated with a pharmaceutically acceptable carrier in accordance with the usual pharmaceutical practice. Examples of the pharmaceutically acceptable carrier include excipients, binders, diluents, additives, fragrances, buffering agents, thickeners, colorants, stabilizers, emulsifiers, dispersants, suspending agents, preservatives, etc. Specific examples of the carrier include magnesium carbonate, magnesium stearate, talc, sugar, lactose, pectin, dextrin, starch, gelatin, tragacanth, methylcellulose, sodium carboxymethyl cellulose, low melting wax, cacao butter, etc.

Preferably, the oral solid preparations (tablets, pills, capsules, powders, granules, etc.) are produced by mixing the active ingredient with an additive, such as an excipient (lactose, mannitol, glucose, microcrystalline cellulose, starch, etc.), a binder (hydroxypropyl cellulose, polyvinylpyrrolidone, magnesium aluminometasilicate, etc.), a disintegrant (calcium carboxymethyl cellulose etc.), a lubricant (magnesium stearate etc.), a stabilizer, a solubilizer (glutamic acid, aspartic acid, etc.) and/or the like, and processing the mixture into the dosage form of interest in the usual manner. If needed, the oral solid preparations may be covered with a coating material (sucrose, gelatin, hydroxypropyl cellulose, hydroxypropyl methylcellulose phthalate, etc.), or alternatively, the oral solid preparations may be covered with two or more coating layers.

The oral liquid preparations (solutions, suspensions, emulsions, syrups, elixirs, etc.) can be produced by dissolving, suspending or emulsifying the active ingredient in a commonly used diluent (purified water, ethanol, a mixture of them, etc.). The oral liquid preparations may further comprise a wetting agent, a suspending agent, an emulsifier, a sweetener, a flavoring agent, a fragrance, a preservative, a buffering agent and/or the like.

The parenteral preparations are, for example, external preparations for skin. The external preparations for skin can be in the form of solutions, creams, ointments, gels, aerosols, etc., but the dosage forms are not limited thereto. Other dosage forms suitable for external use may also be employed.

The external preparations for skin can comprise, as needed, water, a lower alcohol, a solubilizer, a surfactant, an emulsion stabilizer, a gelatinizing agent, an adhesive and/or other ingredients, as well as a commonly used base appropriate for the desired dosage form. The external preparations for skin may further comprise, as appropriate, a vasodilator, a corticosteroid, a moisturizer, a microbicide, a cooling agent, a vitamin, a fragrance, a pigment and/or the like in accordance with the intended use unless the additives impair the effects of the present invention.

Other examples of the parenteral preparations include injections. The injections include solutions, suspensions, emulsions, and solid injectable preparations that are intended to be dissolved or suspended in a solvent at the time of use. The injections can be produced by dissolving, suspending or emulsifying the active ingredient in a solvent. Examples of the solvent include distilled water for injection, physiological saline, vegetable oils, alcohols such as propylene glycol, polyethylene glycols and ethanol, and a combination thereof. The injections may further comprise a stabilizer, a solubilizer (glutamic acid, aspartic acid, polysorbate 80 (registered trademark), etc.), a suspending agent, an emulsifier, a soothing agent, a buffering agent, a preservative, and/or the like. The injections are sterilized in the final step of the production process or produced in an aseptic manner. Alternatively, sterile solid preparations, for example, lyophilized preparations may be produced for use as injections. Such sterile solid preparations are intended to be dissolved in a sterilized or aseptic distilled water for injection or another solvent at the time of use.

The present invention provides a medicament for promoting hair regrowth. The medicament of the present invention may be any type of medicament as long as it comprises the above hair regrowth promoter of the present invention. The medicament of the present invention may be in the form of an oral solid preparation (a tablet, a pill, a capsule, a powder, granules, etc.), an oral liquid preparation, etc. These preparations can be formulated in the same manner as above.

The present invention provides a dietary supplement for promoting hair regrowth. The dietary supplement of the present invention may be any type of dietary supplement as long as it comprises the above hair regrowth promoter of the present invention. The dietary supplement of the present invention may be in the form of an oral solid preparation (a tablet, a pill, a capsule, a powder, granules, etc.), an oral liquid preparation, etc. These preparations can be formulated in the same manner as above.

The present invention is intended to provide not a food or drink itself but a food or drink product to which the egg-yolk protein hydrolysate for promoting hair regrowth has been added or which has an increased content of the egg-yolk protein hydrolysate. The food or drink product of the present invention may be any type of food or drink product as long as it comprises the above hair regrowth promoter of the present invention. Examples of the food or drink product include health foods, functional foods, foods for specified health use, and foods for the sick. The form of the food or drink product is not particularly limited, and the food or drink product may be in the form of a processed food or drink, such as a liquid diet, a low residue diet, and an elemental diet, or an energy drink. Examples of the food or drink product include drinks such as tea drink, soft drink, carbonated drink, nutritional drink, fruit juice and lactic drink; noodles such as buckwheat noodle, wheat noodle, Chinese noodle and instant noodle; sweets and bakery such as hard candy, candy, chewing gum, chocolate, snack, biscuit, jelly, jam, cream, baked sweets and bread; processed fishery and livestock products such as fish cake, ham and sausage; dairy products such as processed milk and fermented milk; fats, oils and processed fat and oil products such as vegetable oil, tempura oil, margarine, mayonnaise, shortening, whipped cream and dressing; seasonings such as sauce and dipping sauce; retort pouch food products such as curry, stew, rice bowl, rice porridge and rice soup; and frozen desserts such as ice cream, sherbet and shaved ice. The food or drink product of the present invention includes a food for specified health use, a dietary supplement, a supplemental food, and a functional food, each bearing a statement indicating hair regrowth-promoting effect. The food or drink product of the present invention may comprise a pharmaceutical excipient, such as lactose, starch, crystalline cellulose, and sodium phosphate.

The present invention is intended to provide not a food or drink itself but a food additive for promoting hair regrowth. The food additive of the present invention may be any type of food additive as long as it comprises the above hair regrowth promoter of the present invention. The form of the food additive of the present invention is not particularly limited, and may be, for example, a liquid, a paste, a powder, flakes, granules, etc. The food additive of the present invention includes an additive for drinks. The food additive of the present invention can be produced in accordance with a conventional production process for food additives.

The present invention provides an animal feed for promoting hair regrowth. The animal feed of the present invention may be any type of animal feed as long as it comprises the above hair regrowth promoter of the present invention. Examples of the animal feed include feeds for domestic animals, such as cattle, horses, pigs, sheep, goats, llamas, alpacas, camels, rabbits, minks, foxes, chinchillas, geese, and ducks; feeds for companion animals, such as dogs and cats; etc. The animal feed of the present invention can be produced with the addition of the hair regrowth promoter of the present invention etc., in accordance with a conventional production process for animal feeds.

The egg-yolk protein hydrolysate as an active ingredient of the hair regrowth promoter of the present invention is a substance present in an egg yolk, which already has a long history as a food. The egg-yolk protein hydrolysate is therefore highly safe and has mild effects, and hence can be administered or used for a long period of time. The egg-yolk protein hydrolysate as an active ingredient is a multifunctional substance with various effects. A combination use of the egg-yolk protein hydrolysate with another active ingredient for promoting hair regrowth is expected to achieve additive effect or synergistic effect. Examples of the additional active ingredient for promoting hair regrowth include minoxidil and finasteride.

The present invention also includes a method for promoting hair regrowth, the method comprising administering an effective amount of the egg-yolk protein hydrolysate to a human in need of promotion of hair regrowth. The present invention further includes a non-therapeutic method for promoting hair regrowth, the method comprising orally administering the egg-yolk protein hydrolysate to a human in need of promotion of hair regrowth. The term "non-therapeutic" refers to any means other than medical practice, i.e., other than therapeutic treatments to human or animal bodies.

The present invention also includes a method for promoting hair regrowth, the method comprising administering an effective amount of the hair regrowth promoter of the present invention to an animal in need of promotion of hair regrowth. The animal is not particularly limited, and may be, for example, a human, a non-human mammal, etc. Examples of the non-human mammal include, but are not limited to, cattle, horses, pigs, sheep, goats, llamas, alpacas, camels, rabbits, minks, foxes, chinchillas, geese, ducks, etc.

The present invention also includes use of the hair regrowth promoter of the present invention for promotion of hair regrowth.

The present invention further includes the hair regrowth promoter of the present invention for use in promotion of hair regrowth.

EXAMPLES

The present invention will be described in more detail below with reference to Examples, but the present invention is not limited thereto.

Example 1: Production of Egg-Yolk Protein Hydrolysate (1) Preparation of Defatted Egg Yolk To 1 kg of egg-yolk powder was added 5 L of ethanol, the mixture was stirred with a blender for 30 minutes, and the resulting solids were collected. This procedure was repeated three times for fat removal from the egg yolk. The collected solids were air-dried to give 568 g of defatted egg yolk powder.

(2) Preparation of Egg-Yolk Protein Hydrolysate

To 500 g of the defatted egg yolk powder prepared in the above (1) were added 2.5 kg of water and 25 g of Alcalase (trade name) (protease from *Bacillus licheniformis*) produced by Novozymes A/S. The pH of the mixture was adjusted to 7, and the enzyme reaction was allowed to proceed at 55° C. for 3 hours. The reaction mixture was heated at 80° C. for 15 minutes to inactivate the enzyme, and centrifuged at 3000×g for 20 minutes to remove insoluble matter. After filtration, the filtrate was spray-dried to give about 140 g of egg-yolk protein hydrolysate.

The molecular weight analysis of the egg-yolk protein hydrolysate was performed by gel filtration chromatography under the following conditions.

Column: Diol 60 (trade name) (6.0×300 mm) (YMC Co., Ltd.)
Eluent: 0.2 M potassium phosphate buffer, 0.2 M NaCl (pH 6.9)/acetonitrile (70:30)
Flow rate: 0.7 mL/min
Detection wavelength: 280 nm The results of the molecular weight analysis are shown in FIG. 1. As shown in FIG. 1, the molecular weight distribution of the egg-yolk protein hydrolysate of Example 1 was such that the peak area percentage for a molecular weight range of 100 to 20,000 was about 90% of the total area of all the peaks of proteins, peptides and amino acids.

Example 2: Animal Testing (Assessment of Hair Growth-Promoting Effect in C3H Mice)

SPF C3H/HeN Slc (male) mice available from Japan SLC, Inc. were used for the test. The animals were randomly divided into test groups so that the mean body weight was approximately equal between groups. The mice were housed five per cage at room temperature (25° C.) under a 12-hour light-dark cycle.

The mice at six weeks old purchased from the vendor were preliminarily bred for one week for acclimation to the test environment. The dorsal region of the mice at an age of seven weeks old was shaved with a safety razor to remove the hair.

Until the start of the test, the mice were fed with free access to a solid CRF-1 feed (Oriental Yeast Co., Ltd.) and tap water as drinking water.

The test conditions are shown in Table 1.

TABLE 1

| Type of feed | Test group | Dose (mg/kg) | Number of animals |
| --- | --- | --- | --- |
| Negative control | Regular feed (CRF-1) | 0 | 10 |
| Test sample | Feed mixed with egg-yolk protein hydrolysate (low dose) | 10 | 10 |
| | Feed mixed with egg-yolk protein hydrolysate (medium dose) | 100 | 10 |
| | Feed mixed with egg-yolk protein hydrolysate (high dose) | 1000 | 10 |

The test was started three days after shaving. Specifically, the mice in the test sample administration groups were fed with a mixed feed of the regular feed (CRF-1) and the egg-yolk protein hydrolysate in the dose indicated in Table 1, whereas the mice in the negative control group were fed with the regular feed (CRF-1).

On the final observation day (Day 17), the mice in the test and control groups were anesthetized and euthanized. The mice were fixed on a photography table and the shaved region was photographed. The region covered with new hair was quantified from the photographs using an image analysis software to determine whether the test sample had hair regrowth-promoting effect.

Figure 2:
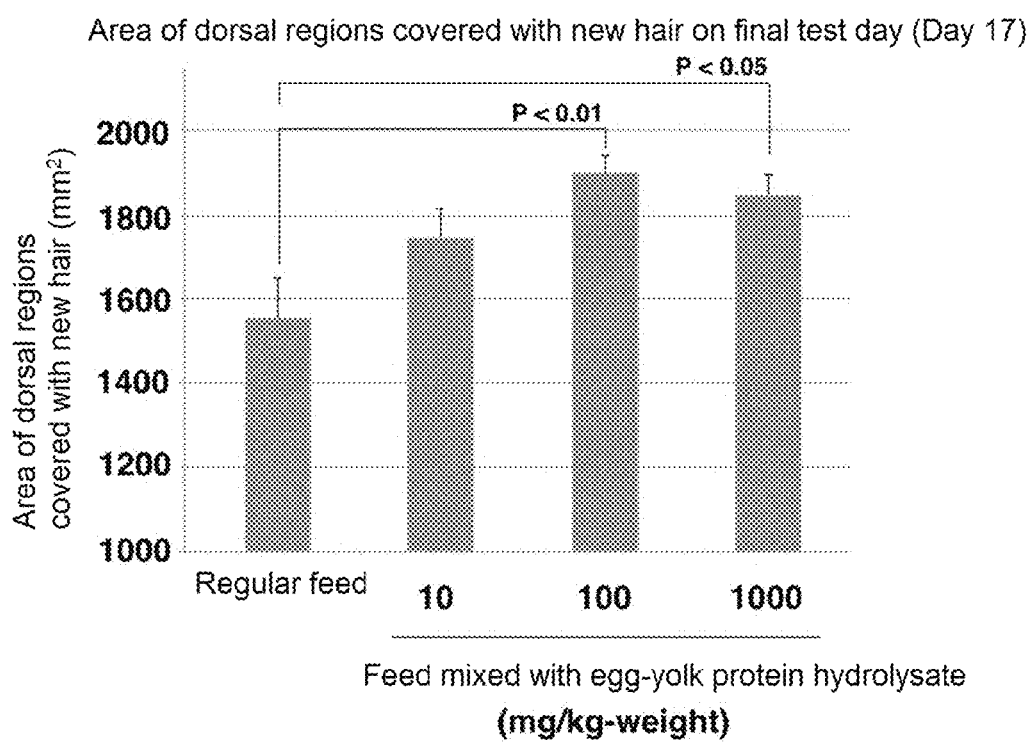
FIG. 2 is a graph showing the areas of dorsal regions covered with new hair in mice on Day 17 of feeding with a feed mixed with an egg-yolk protein hydrolysate.
Figure 3:
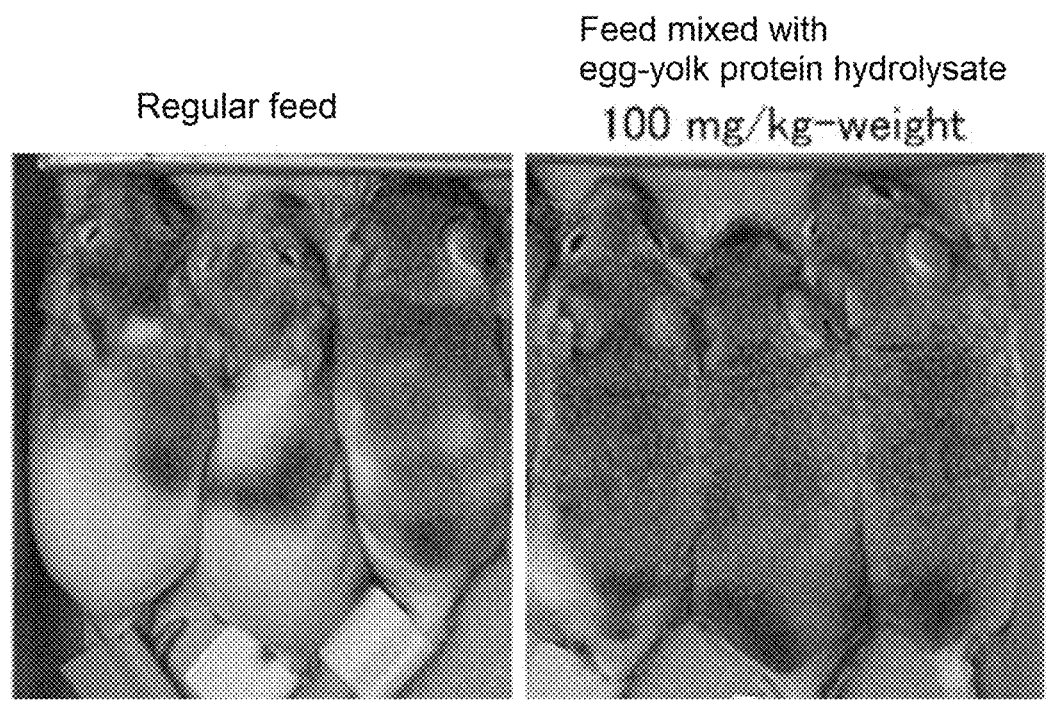
FIG. 3 is photographs showing the comparison of the appearance of dorsal regions covered with new hair in mice fed with a regular feed and in mice fed with a feed mixed with an egg-yolk protein hydrolysate on day 17 of feeding.

FIG. 2 shows the areas of the dorsal regions covered with new hair in the mice on Day 17 of feeding with the feed mixed with the egg-yolk protein hydrolysate. FIG. 3 shows the comparison of the appearance of the dorsal regions covered with new hair in the mice fed with the regular feed and in the mice fed with the feed mixed with the egg-yolk protein hydrolysate on day 17 of feeding. Hair regrowth in the groups fed with the egg-yolk protein hydrolysate was promoted in a manner dependent on the amount of intake of the egg-yolk protein hydrolysate. A significant difference was observed at a dose of 100 mg/kg or more.

Example 3: Cell Test (Measurement of Growth Factors in Hair Follicle Dermal Papilla Cells)

(1) Measurement of the Production Levels of Vascular Endothelial Growth Factor (VEGF)

Human hair follicle dermal papilla cells (HFDPCs) (Cell Applications, Inc.) in the logarithmic growth phase were suspended at $3\times10^4$ cells/mL in hair follicle dermal papilla cell growth medium (PCGM) (Cell Applications, Inc.). One milliliter of the suspension was seeded in a 24-well (collagen-coated) plate and the cells were precultured.

After the growth of the cells was observed under a microscope, all the medium was replaced with a fresh medium.

Test samples were separately added to the medium and incubation was started. Specifically, the test samples were prepared by dissolving the egg-yolk protein hydrolysate in PBS (−) at 100 mg/mL and 500 mg/mL, and added to the medium at 1% of the total volume of the medium (final concentration: 1 mg/mL and 5 mg/mL, respectively). As a model drug for promotion of the production of VEGF, minoxidil (Sigma-Aldrich Co. LLC.) was used. Minoxidil was dissolved in ethanol at 3 mM and added to the medium at 1% of the total volume of the medium (final concentration: 30 μM).

After two days' incubation, the VEGF concentration in the medium was measured using Human VEGF ELISA kit (R&D Systems).

Figure 4:
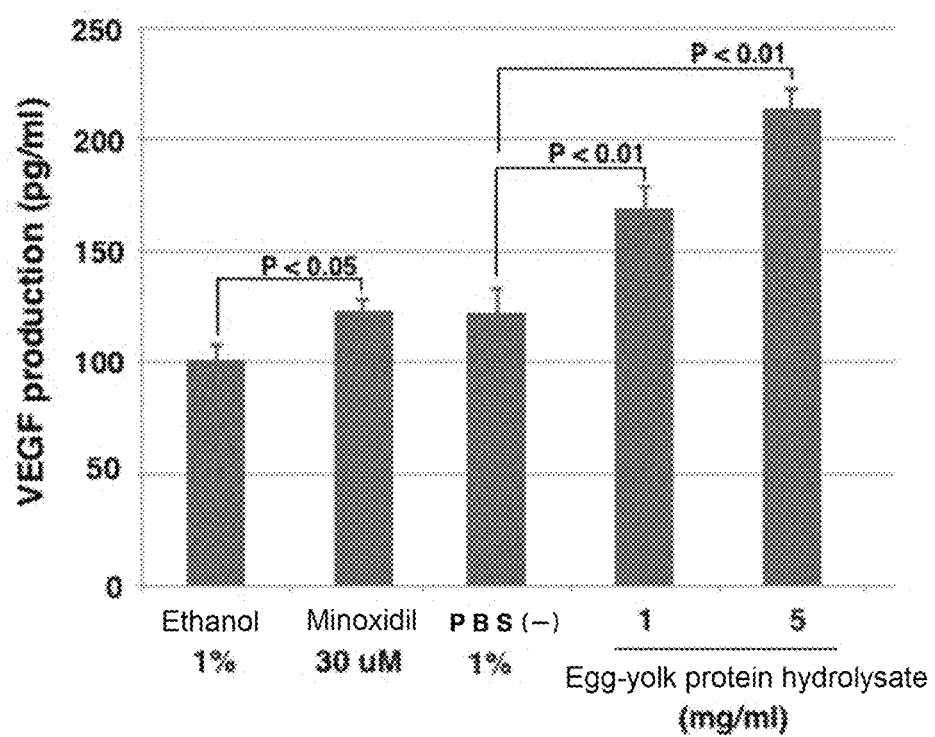
FIG. 4 is a graph showing the VEGF production-promoting effect of an egg-yolk protein hydrolysate on hair follicle dermal papilla cells.

The results are shown in FIG. 4. The amounts of VEGF secreted from the hair follicle dermal papilla cells into the medium increased in a manner dependent on the concentration of the egg-yolk protein hydrolysate added.

(2) Measurement of the mRNA Expression Levels of Fibroblast Growth Factor-7 (FGF-7)

Human hair follicle dermal papilla cells in the logarithmic growth phase were suspended at $3\times10^4$ cells/mL in DMEM medium (containing 10% serum). One milliliter of the suspension was seeded in a 24-well (collagen-coated) plate and the cells were precultured.

All the medium was removed and serum-free DMEM medium was added. Immediately after that, a test sample was added to the medium, and the cells were incubated in a $CO_2$ incubator for 2 hours. Specifically, the test sample was prepared by dissolving the egg-yolk protein hydrolysate in PBS (−) at 100 mg/mL, and added to the medium at 1% of the total volume of the medium (final concentration: 1 mg/mL). As an inducer of the expression of FGF-7, adenosine (Wako Pure Chemical Industries, Ltd.) was used. Adenosine was dissolved in DMSO at 10 mM and added to the medium at 1% of the total volume of the medium (final concentration: 100 μM).

After the incubation, all the medium was removed, and immediately after that, the cells were lysed in 1 mL of ISOGEN II (NIPPON GENE), and total RNA was extracted following the manufacturer's recommended protocol. cDNA was synthesized using the total RNA as a template with PrimeScript RT reagent Kit (Takara) following the manufacturer's recommended protocol. Real-time PCR was performed using the reaction mixture as a template with SYBR Premix EX Taq (Takara) and LightCycler 480 (Roche) following the manufacturer's recommended protocols. The nucleotide sequences of the primers used in the PCR are shown in Table 2.

TABLE 2

| | Forward | Reverse |
|---|---|---|
| FGF-7 | TCTGTCGAACACAGTGGTACCTG AG (SEQ ID NO: 1) | AGTACCTTTAGTCCTGTCAC CG (SEQ ID NO: 2) |
| GAPDH | GCACCGTCAAGGCTGAGAAC (SEQ ID NO: 3) | ATGGTGGTGAAGACGCCAGT (SEQ ID NO: 4) |

Figure 5:
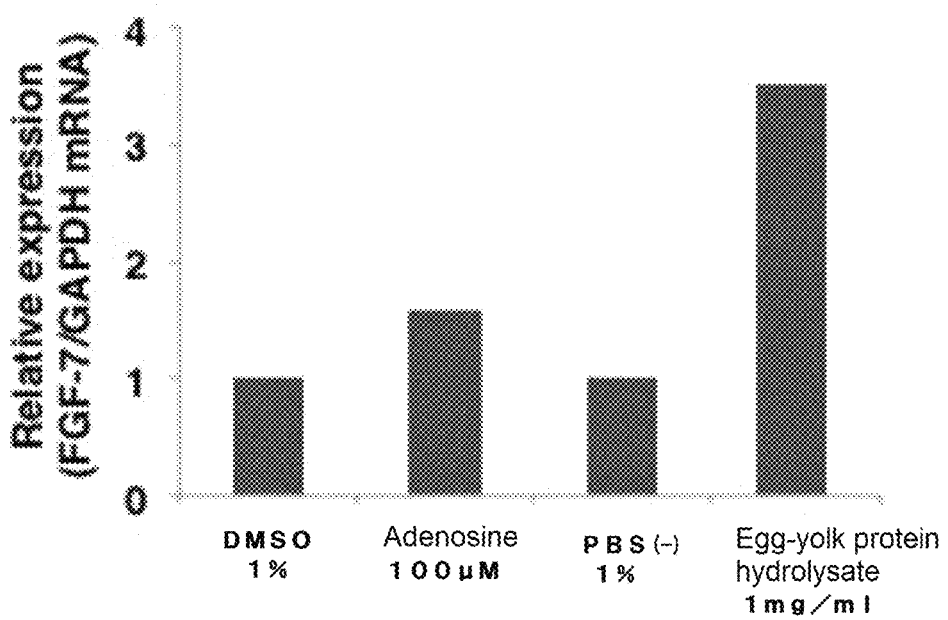
FIG. 5 is a graph showing the FGF-7 mRNA expression-enhancing effect of an egg-yolk protein hydrolysate on hair follicle dermal papilla cells.

The results are shown in FIG. 5. The addition of the egg-yolk protein hydrolysate to the medium increased the mRNA levels of FGF-7.

(3) Measurement of the mRNA Expression Levels of Insulin-Like Growth Factor (IGF-1)

Human hair follicle dermal papilla cells in the logarithmic growth phase were suspended at $3\times10^4$ cells/mL in DMEM medium (containing 10% serum). One milliliter of the suspension was seeded in a 24-well (collagen-coated) plate and the cells were precultured.

All the medium was removed and serum-free DMEM medium was added. Immediately after that, a test sample was added to the medium, and the cells were incubated in a $CO_2$ incubator for 4 hours. Specifically, the test sample was prepared by dissolving the egg-yolk protein hydrolysate in PBS (−) at 100 mg/mL, and added to the medium at 1% of the total volume of the medium (final concentration: 1 mg/mL). As an inducer of the expression of IGF-1, adenosine was used. Adenosine was dissolved in DMSO at 10 mM and added to the medium at 1% of the total volume of the medium (final concentration: 100 μM).

After the incubation, all the medium was removed, and immediately after that, the cells were lysed in 1 mL of ISOGEN II (NIPPON GENE), and total RNA was extracted following the manufacturer's recommended protocol. cDNA was synthesized using the total RNA as a template with PrimeScript RT reagent Kit (Takara) following the manufacturer's recommended protocol. Real-time PCR was performed using the reaction mixture as a template with SYBR Premix EX Taq (Takara) and LightCycler 480 (Roche) following the manufacturer's recommended protocols. The nucleotide sequences of the primers used in the PCR are shown in Table 3.

TABLE 3

| | Forward | Reverse |
|---|---|---|
| IGF-1 | TTTCAAGCCACCCATTGACC (SEQ ID NO: 5) | GCGGGTACAAGATAAATATC CAAAC (SEQ ID NO: 6) |
| GAPDH | GCACCGTCAAGGCTGAGAAC (SEQ ID NO: 3) | ATGGTGGTGAAGACGCCAGT (SEQ ID NO: 4) |

Figure 6:
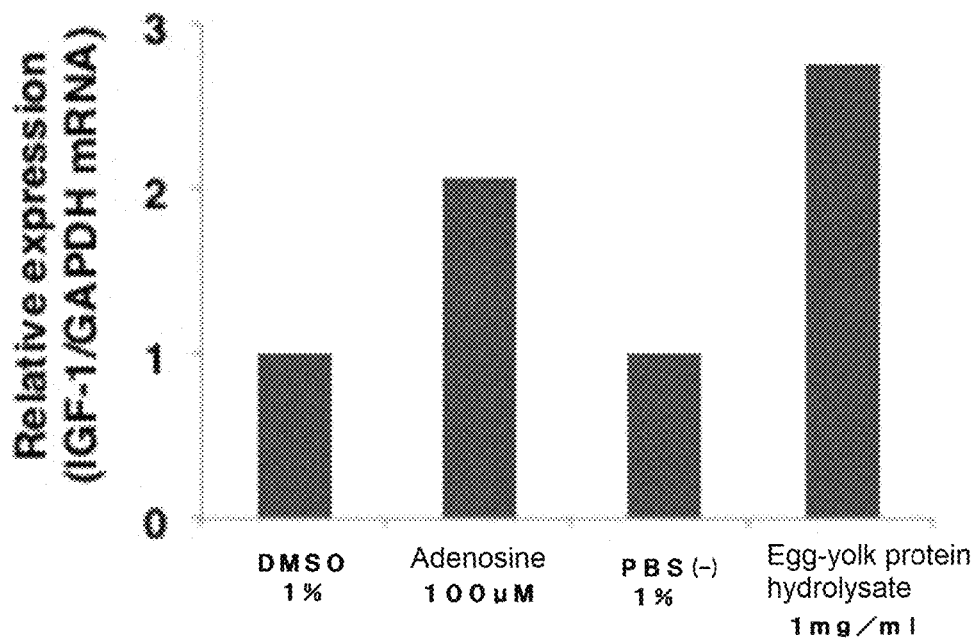
FIG. 6 is a graph showing the IGF-1 mRNA expression-enhancing effect of an egg-yolk protein hydrolysate on hair follicle dermal papilla cells.

The results are shown in FIG. 6. The addition of the egg-yolk protein hydrolysate to the medium increased the mRNA levels of IGF-1.

Example 4: Animal Testing (Assessment of Anagen Induction Effect in C57BL/6 Mice)

C57BL/6 (female) mice available from Charles River Laboratories Japan, Inc. were used for the test. The animals were randomly divided into test groups so that the mean body weight was approximately equal between groups. The mice were housed five per cage at room temperature (25° C.) under a 12-hour light-dark cycle.

The mice at six weeks old purchased from the vendor were preliminarily bred for one week for acclimation to the test environment. A commercially available hair removal cream was applied to the dorsal region of the mice at an age of seven weeks old to remove the hair.

Until the start of the test, the mice were fed with free access to a solid CRF-1 feed (Oriental Yeast Co., Ltd.) and tap water as drinking water.

The test conditions are shown in Table 4.

TABLE 4

| Type of feed | Test group | Dose (mg/kg) | Number of animals |
|---|---|---|---|
| Negative control | Feed mixed with casein | 100 | 5 |
| Test sample | Feed mixed with egg-yolk protein hydrolysate | 100 | 5 |

The hair of the 7-week-old C57BL/6 mice was in the telogen phase of the hair cycle, but due to the stimulation of hair removal, the hair gradually entered into the anagen phase. The test was started three days after the hair removal. Specifically, the mice in the test sample administration group were fed with a mixed feed of the regular feed (CRF-1) and the egg-yolk protein hydrolysate in the dose indicated in Table 4, whereas the mice in the negative control group were fed with the regular feed (CRF-1) mixed with casein.

On the final observation day (Day 9 of administration), the mice in the test and control groups were anesthetized and euthanized. The dorsal skin was shaved with an electric shaver to remove the hair, and the skin on each side of the median line was harvested (from the base of the ears towards the rump). The harvested skin was fixed in 10% neutral buffered formalin solution and paraffin-embedded. The specimens were sectioned parallel to the body axis into 4-μm slices, and were HE stained. On the stained sections, 500 hair follicles were examined for each group, and the frequency of anagen VI hair follicles was determined.

The group with oral administration of the egg-yolk protein hydrolysate showed a higher frequency of anagen VI hair follicles than the group with oral administration of casein. The results indicated that oral administration of the egg-yolk protein hydrolysate induced the maturation of anagen hair follicles, thereby promoting hair regrowth.

Example 5: Animal Testing (Assessment of Hair Growth-Promoting Effect on Androgen-Induced Telogen)

C57BL/6 (female) mice available from Charles River Laboratories Japan, Inc. were used for the test. The animals were randomly divided into test groups so that the mean body weight was approximately equal between groups. The mice were housed three per cage at room temperature (25° C.) under a 12-hour light-dark cycle.

The mice at six weeks old purchased from the vendor were preliminarily bred for one week for acclimation to the test environment. A commercially available hair removal cream was applied to the dorsal region of the mice at an age of seven weeks old to remove the hair.

Until the start of the test, the mice were fed with free access to a solid CRF-1 feed (Oriental Yeast Co., Ltd.) and tap water as drinking water.

The hair of the 7-week-old C57BL/6 mice was in the telogen phase of the hair cycle, but due to the stimulation of hair removal, the hair gradually entered into the anagen phase. This transition in the hair cycle was hampered by administration of an androgen after the hair removal. Specifically, dihydrotestosterone (DHT) was dissolved at 2 mg/mL in phosphate buffered saline containing 20% by mass of ethanol, and 100 μL of the solution was subcutaneously injected into the hair removal region every other day. From two days after the hair removal, the mixed feeds indicated in Table 5 were given with free access thereto.

TABLE 5

| DHT administration | Test group | Mixing ratio | Number of animals |
|---|---|---|---|
| No | Feed mixed with casein | 2% by mass | 3 |
| Yes | Feed mixed with casein | 2% by mass | 3 |
| Yes | Feed mixed with egg-yolk protein hydrolysate | 2% by mass | 3 |

Figure 7:
FIG. 7 is photographs showing the comparison of the appearance of dorsal regions covered with new hair in telogen-induced mice fed with a regular feed and in telogen-induced mice fed with a feed mixed with an egg-yolk protein hydrolysate on day 14 of feeding.

On the final observation day (Day 14 of administration), the mice in the test and control groups were anesthetized and fixed on a photography table, and the hair removal region was photographed. As shown in FIG. 7, the dorsal skin of the mice in the casein-containing feed group with no DHT administration appeared to be blackened, and hair regrowth was confirmed. However, the blackening of the dorsal skin was inhibited by DHT administration. In contrast to the casein-containing feed group with DHT administration, the blackened region of the skin increased in the egg-yolk protein hydrolysate-containing feed group, and hair regrowth was confirmed. The results indicated that oral administration of the egg-yolk protein hydrolysate induced the transition from telogen to anagen, thereby promoting hair regrowth.

The present invention is not limited to each of the embodiments and Examples described above, and various modifications are possible within the scope of the claims. Embodiments obtainable by appropriately combining the technical means disclosed in the different embodiments of the present invention are also included in the technical scope of the present invention.

INDUSTRIAL APPLICABILITY

The present invention is useful as a hair regrowth promoter.

The invention claimed is:

1. A method for promoting hair regrowth, the method comprising orally administering an egg-yolk protein hydrolysate to a human in need of promotion of hair regrowth, to promote hair regrowth.

2. A method for promoting hair regrowth, the method comprising administering an effective amount of a hair regrowth promoter comprising an egg-yolk protein hydrolysate as an active ingredient to an animal in need of promotion of hair regrowth to promote hair regrowth.

3. The method according to claim 2, wherein the hair regrowth promoter is contained in a food for specified health use, a dietary supplement, a supplemental food, or a functional food, bearing a statement indicating hair regrowth promoting effect.

4. The method according to claim 2, wherein the hair regrowth promoter has a promoting effect on the production of a growth factor in hair follicle dermal papilla cells.

5. The method according to claim 4, wherein the growth factor is one or more selected from the group consisting of vascular endothelial growth factor (VEGF), fibroblast growth factor-7 (FGF-7) and insulin-like growth factor-1 (IGF-1).

6. The method according to claim 2, wherein the hair regrowth promoter is in a form of an oral preparation.

7. The method according to claim 2, wherein the hair regrowth promoter is in a form of a medicament for promoting hair regrowth.

8. The method according to claim 2, wherein the hair regrowth promoter is in a form of a dietary supplement for promoting hair regrowth.

9. The method according to claim 2, wherein the hair regrowth promoter is in a form of a food additive for promoting hair regrowth.

10. The method according to claim 2, wherein the hair regrowth promoter is in a form of a parenteral preparation.

11. The method according to claim 1, wherein the egg-yolk protein hydrolysate is orally administered to a human in need of promotion of hair growth in addition to hair regrowth to promote hair growth in addition to hair regrowth.

12. The method according to claim 2, wherein an effective amount of a hair growth promoter comprising an egg-yolk protein hydrolysate is administered to an animal in need of promotion of hair growth in addition to hair regrowth to promote hair growth in addition to hair regrowth.

13. The method according to claim 12, wherein the hair growth promoter is contained in a food for specified health use, a dietary supplement, a supplemental food, or a functional food, bearing a statement indicating hair growth promoting effect.

14. The method according to claim 12, wherein the hair growth promoter has a promoting effect on the production of a growth factor in hair follicle dermal papilla cells.

15. The method according to claim 14, wherein the growth factor is one or more selected from the group consisting of vascular endothelial growth factor(VEGF), fibroblast growth factor-7 (FGF-7) and insulin-like growth factor 1 (IGF-1).

16. The method according to claim 12, wherein the hair growth promoter is in a form of an oral preparation.

17. The method according to claim 12, wherein the hair growth promoter is in a form of a medicament for promoting hair growth.

18. The method according to claim 12, wherein the hair growth promoter is in a form of dietary supplement for promoting hair growth.

19. The method according to claim 12, wherein the hair growth promoter is in a form of a food additive for promoting hair growth.

20. The method according to claim 12, wherein the hair growth promoter is in a form of a parenteral preparation.

* * * * *

SEQUENCE LISTING

<160> NUMBER OF SEQ ID NOS: 6

<210> SEQ ID NO 1
<211> LENGTH: 25
<212> TYPE: DNA
<213> ORGANISM: Artificial Sequence

```
<220> FEATURE:
<223> OTHER INFORMATION: primer

<400> SEQUENCE: 1
tctgtcgaac acagtggtac ctgag                                              25

<210> SEQ ID NO 2
<211> LENGTH: 22
<212> TYPE: DNA
<213> ORGANISM: Artificial Sequence
<220> FEATURE:
<223> OTHER INFORMATION: primer

<400> SEQUENCE: 2 agtacccttta gtcctgtcac cg                                                22

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
gcaccgtcaa ggctgagaac                                                    20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
atggtggtga agacgccagt                                                    20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
tttcaagcca cccattgacc                                                    20

<210> SEQ ID NO 6
<211> LENGTH: 25
<212> TYPE: DNA
<213> ORGANISM: Artificial Sequence
<220> FEATURE:
<223> OTHER INFORMATION: primer

<400> SEQUENCE: 6
gcgggtacaa gataaatatc caaac                                              25
```